United States Patent
Gaffney et al.

(10) Patent No.: US 7,074,956 B2
(45) Date of Patent: Jul. 11, 2006

(54) HYDROTHERMALLY SYNTHESIZED MO-V-M-X OXIDE CATALYSTS FOR THE SELECTIVE OXIDATION OF HYDROCARBONS

(75) Inventors: Anne Mae Gaffney, West Chester, PA (US); Ruozhi Song, Wilmington, DE (US)

(73) Assignee: Rohm and Haas Company, Philadelphia, PA (US)

( * ) Notice: Subject to any disclaimer, the term of this patent is extended or adjusted under 35 U.S.C. 154(b) by 124 days.

(21) Appl. No.: 10/806,582

(22) Filed: Mar. 23, 2004

(65) Prior Publication Data

US 2004/0181084 A1    Sep. 16, 2004

Related U.S. Application Data

(62) Division of application No. 10/165,892, filed on Jun. 10, 2002, now Pat. No. 6,746,983.

(60) Provisional application No. 60/299,213, filed on Jun. 18, 2001.

(51) Int. Cl.
*C07C 51/16* (2006.01)
(52) U.S. Cl. ........................................ 562/547; 562/549
(58) Field of Classification Search ................ None
See application file for complete search history.

(56) References Cited

U.S. PATENT DOCUMENTS

| | | |
|---|---|---|
| 5,281,745 A | 1/1994 | Ushikubo et al. |
| 5,380,933 A | 1/1995 | Ushikubo et al. |
| 6,043,185 A | 3/2000 | Cirjak et al. |

FOREIGN PATENT DOCUMENTS

| | | |
|---|---|---|
| JP | 7-53448 | 2/1995 |
| JP | 2000-143244 | 5/2000 |

OTHER PUBLICATIONS

Ueda, et al., "Hydrothermal Synthesis of Mo-V-M-O Complex Metal Oxide Catalysts Active For Partial Oxidation of Ethane", Chem. Commun., 1999, pp. 517-518.

Ueda, et al., "Selective Oxidation of Light Alkanes Over Mo-Based Oxide Catalysts", Res. Chem. Intermed., vol. 26, No. 2, pp. 137-144(2000).

Watanabe, et al., "New Synthesis Route for Mo-V-Nb-Te Mixed Metal Oxides For Propane Ammoxidation", Applied Catalysis A: General, 194-195, pp. 479-485 (2000).

Ueda, et al., "Selective Oxidation of Light Alkanes Over Hydrothermally Synthesized Mo-V-M-O (M=Al, Ga, Bi, Sb and Te) Oxide Catalysts", Applied Catalysis A: General, 200, pp. 135-143 (2000).

Chen, et al., "Selective Oxidation of Ethane Over Hydrothermally Synthesized Mo-V-Al-Ti Oxide Catalyst", Catalysis Today, 64, pp. 121-128(2001).

Derwent Publications Ltd., London, GB; Class A41, AN 2000-256515, XP002210373 & Translation of Japanese Language Abstract of WO 0012209A.

*Primary Examiner*—Paul A. Zucker
(74) *Attorney, Agent, or Firm*—Marcella Bodner; Alan Holler

(57) ABSTRACT

Hydrothermally synthesized catalysts comprising a mixed metal oxide are utilized to produce unsaturated carboxylic acids by the vapor phase oxidation of an alkane, or a mixture of an alkane and an alkene, in the presence thereof; or to produce unsaturated nitriles by the vapor phase oxidation of an alkane, or a mixture of an alkane and an alkene, and ammonia in the presence thereof.

6 Claims, No Drawings

HYDROTHERMALLY SYNTHESIZED MO-V-M-X OXIDE CATALYSTS FOR THE SELECTIVE OXIDATION OF HYDROCARBONS

This non-provisional application is a divisional of non-provisional U.S. patent application Ser. No. 10/165,892 filed Jun. 10, 2002, now granted as U.S. No. 6,746,983, benefit of which is claimed under 35 U.S.C. § 120 and which in turn claims benefit under 35 U.S.C. § 119(e) of U.S. provisional Application No. 60/299,213, filed Jun. 18, 2001, priority benefit of which is also claimed for the present application.

The present invention relates to a catalyst for the oxidation of alkanes, or a mixture of alkanes and alkenes, to their corresponding unsaturated carboxylic acids by vapor phase catalytic oxidation; to a method for making the catalyst; and to a process for the vapor phase catalytic oxidation of alkanes, or a mixture of alkanes and alkenes, to their corresponding unsaturated carboxylic acids using the catalyst. The present invention also relates to a process for the vapor phase catalytic oxidation of alkanes, or a mixture of alkanes and alkenes, in the presence of ammonia, to their corresponding unsaturated nitriles using the catalyst.

Nitriles, such as acrylonitrile and methacrylonitrile, have been industrially produced as important intermediates for the preparation of fibers, synthetic resins, synthetic rubbers, and the like. The most popular method for producing such nitrites is to subject an olefin such as propene or isobutene to a gas phase catalytic reaction with ammonia and oxygen in the presence of a catalyst at a high temperature. Known catalysts for conducting this reaction include a Mo—Bi—P—O catalyst, a V—Sb—O catalyst, an Sb—U—V—Ni—O catalyst, a Sb—Sn—O catalyst, a V—Sb—W—P—O catalyst and a catalyst obtained by mechanically mixing a V—Sb—W—O oxide and a Bi—Ce—Mo—W—O oxide. However, in view of the price difference between propane and propene or between isobutane and isobutene, attention has been drawn to the development of a method for producing acrylonitrile or methacrylonitrile by an ammoxidation reaction wherein a lower alkane, such as propane or isobutane, is used as a starting material, and it is catalytically reacted with ammonia and oxygen in a gaseous phase in the presence of a catalyst.

In particular, U.S. Pat. No. 5,281,745 discloses a method for producing an unsaturated nitrile comprising subjecting an alkane and ammonia in the gaseous state to catalytic oxidation in the presence of a catalyst which satisfies the conditions:

(1) the mixed metal oxide catalyst is represented by the empirical formula

$Mo_a V_b Te_c X_x O_n$ wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron and cerium and, when a=1, b=0.01 to 1.0, c=0.01 to 1.0, x=0.01 to 1.0 and n is a number such that the total valency of the metal elements is satisfied; and (2) the catalyst has X-ray diffraction peaks at the following angles (±0.3°) of 2θ in its X-ray diffraction pattern: 22.1°, 28.2°, 36.2°, 45.2° and 50.0°.

Unsaturated carboxylic acids such as acrylic acid and methacrylic acid are industrially important as starting materials for various synthetic resins, coating materials and plasticizers. Commercially, the current process for acrylic acid manufacture involves a two-step catalytic oxidation reaction starting with a propene feed. In the first stage, propene is converted to acrolein over a modified bismuth molybdate catalyst. In the second stage, acrolein product from the first stage is converted to acrylic acid using a catalyst composed of mainly molybdenum and vanadium oxides. In most cases, the catalyst formulations are proprietary to the catalyst supplier, but, the technology is well established. Moreover, there is an incentive to develop a single step process to prepare the unsaturated acid from its corresponding alkene. Therefore, the prior art describes cases where complex metal oxide catalysts are utilized for the preparation of unsaturated acid from a corresponding alkene in a single step.

Japanese Laid-Open Patent Application Publication No. 07-053448 discloses the manufacture of acrylic acid by the gas-phase catalytic oxidation of propene in the presence of mixed metal oxides containing Mo, V, Te, O and X wherein X is at least one of Nb, Ta, W, Ti, Al, Zr, Cr, Mn, Fe, Ru, Co, Rh, Ni, Pd, Pt, Sb, Bi, B, In, Li, Na, K, Rb, Cs and Ce.

Commercial incentives also exist for producing acrylic acid using a lower cost propane feed. Therefore, the prior art describes cases wherein a mixed metal oxide catalyst is used to convert propane to acrylic acid in one step.

U.S. Pat. No. 5,380,933 discloses a method for producing an unsaturated carboxylic acid comprising subjecting an alkane to a vapor phase catalytic oxidation reaction in the presence of a catalyst containing a mixed metal oxide comprising, as essential components, Mo, V, Te, O and X, wherein X is at least one element selected from the group consisting of niobium, tantalum, tungsten, titanium, aluminum, zirconium, chromium, manganese, iron, ruthenium, cobalt, rhodium, nickel, palladium, platinum, antimony, bismuth, boron, indium and cerium; and wherein the proportions of the respective essential components, based on the total amount of the essential components, exclusive of oxygen, satisfy the following relationships:

0.25<r(Mo)<0.98, 0.003<r(V)<0.5, 0.003<r(Te)<0.5 and 0.003<r(X)<0.5, wherein r(Mo), r(V), r(Te) and r(X) are the molar fractions of Mo, V, Te and X, respectively, based on the total amount of the essential components exclusive of oxygen.

Nonetheless, the prior art continues to seek ways to improve the performance of such mixed metal oxide catalysts.

For example, Ueda, et al., "Hydrothermal Synthesis of Mo—V—M—O Complex Metal Oxide Catalysts Active For Partial Oxidation Of Ethane", Chem. Commun., 1999, pp. 517–518, discloses Mo—V—M—O (M=Al, Fe, Cr or Ti) complex metal oxide catalysts prepared by hydrothermal synthesis, which exhibit activity for the partial oxidation of ethane to ethene and acetic acid.

Ueda, et al., "Selective Oxidation Of Light Alkanes Over Mo-Based Oxide Catalysts", Res, Chem. Intermed., Vol. 26, No. 2, pp. 137–144 (2000) discloses that Anderson-type heteropoly compounds linked with vanadyl cations, $VO^{+2}$, were synthesized by hydrothermal reaction and showed good catalytic activity for the oxidation of ethene to acetic acid.

Watanabe, et al., "New Synthesis Route For Mo—V—Nb—Te Mixed Metal Oxides For Propane Ammoxidation", Applied Catalysis A: General, 194–195, pp. 479–485 (2000) discloses an examination of several methods for preparing Mo—V—Nb—Te mixed oxides. Hydrothermal treatment was shown to give a precursor of an ammoxidation catalyst which shows activity twice as high, after calcination, as the catalyst prepared by the known dry-up method. Mixed oxides prepared by a solid state reaction gave poor catalytic activity.

Ueda, et al., "Selective Oxidation of Light Alkanes Over Hydrothermally Synthesized Mo—V—M—O (M=Al, Ga, Bi, Sb and Te) Oxide Catalysts", Applied Catalysis A: General, 200, pp. 135–143 (2000) discloses selective oxidations of ethane to ethene and acetic acid, and of propane to acrylic acid, carried out over hydrothermally synthesized Mo—V—M—O (M=Al, Ga, Bi, Sb and Te) complex metal oxide catalysts. The solids were classified into two groups, i.e. Mo—V—M—O (M=Al, possibly Ga and Bi) and Mo—V—M—O (M=Sb and Te). The former were moderately active for the partial oxidation of ethane to ethene and acetic acid. The latter were extremely active for the oxidative dehydrogenation and were also active for the partial oxidation of propane to acrylic acid. Grinding of the catalysts, after heat treatment at 600° C. in $N_2$, increased the conversion of propane and enhanced the selectivity to acrylic acid.

Chen, et al., "Selective Oxidation Of Ethane Over Hydrothermally Synthesized Mo—V—Al—Ti Oxide Catalyst", Catalysis Today, 64, pp. 121–128 (2001) discloses synthesis of a monophasic material, $Mo_6V_2Al_1O_x$, by the hydrothermal method, which shows activity for gas-phase oxidation of ethane to ethene and acetic acid. Addition of titanium to the $Mo_6V_2Al_1O_x$ oxide catalyst resulted in a marked increase of the activity for the ethane selective oxidation.

It has now been found that certain novel mixed metal oxide catalysts, which may be prepared by a hydrothermal synthesis technique, may be utilized for the partial oxidation of an alkane, or a mixture of an alkane and an alkene, to produce an unsaturated carboxylic acid; or for the ammoxidation of an alkane, or a mixture of an alkane and an alkene, to produce an unsaturated nitrile.

Thus, in a first aspect, the present invention provides a catalyst comprising a mixed metal oxide having the empirical formula $$Mo_aV_bM_cX_dO_e$$

wherein M is an element selected from the group consisting of Te, Sb and Nb,
wherein X is an element selected from the group consisting of Sc, Y, La, Re, Ir, Cu,
Ag, Au, Zn, Ga, Si, Ge, As, Pb, S, Se, Sn, Bi, F, Cl, Br and I, and
wherein, when a=1, b=0.01 to 1.0, c=0.01 to 1.0, d=0 to 1 and e is dependent on the oxidation state of the other elements;
with the proviso that, when d=0, M is selected from the group consisting of Nb and Te, and
with the further proviso that, when d=0 and M=Te, $0.01 \leq b < 0.50$ or $0.17 < c \leq 1.0$.

In a second aspect, the present invention provides a process for producing a catalyst comprising a mixed metal oxide having the empirical formula $$Mo_aV_bM_cX_dO_e$$

wherein M is an element selected from the group consisting of Te, Sb and Nb,
wherein X is an element selected from the group consiting of Sc, Y, La, Re, Ir, Cu,
Ag, Au, Zn, Ga, Si, Ge, As, Pb, S, Se, Sn, Bi, F, Cl, Br and I, and
wherein, when a=1, b=0.01 to 1.0, c=0.01 to 1.0, d=0 to 1 and e is dependent on the oxidation state of the other elements;
with the proviso that, when d=0, M is selected from the group consisting of Nb and Te, and
with the further proviso that, when d=0 and M=Te, $0.01 \leq b < 0.50$ or $0.17 < c \leq 1.0$, the process comprising:
(i) admixing compounds of elements Mo, V, M and X, as needed, and a solvent comprising water to form a first admixture containing at least 2 but less than all of said elements Mo, V, M and X;
(ii) heating said first admixture at a temperature of from 80° C. to 150° C. for from 5 minutes to 48 hours;
(iii) then, admixing compounds of elements Mo, V, M and X, as needed, with said first admixture to form a second admixture containing elements Mo, V, M and X, in the respective relative atomic proportions a, b, c and d, wherein, when a=1, b=0.01 to 1.0, c=0.01 to 1.0 and d=0 to 1;
(iv) heating said second admixture at a temperature of from 50° C. to 300° C. for from 1 hour to several weeks, in a closed vessel under pressure;
(v) recovering insoluble material from said closed vessel to obtain a catalyst.

In a third aspect, the present invention provides a process for producing an unsaturated carboxylic acid which comprise subjecting an alkane, or a mixture of an alkane and an alkene, to a vapor phase catalytic oxidation reaction in the presence of a catalyst according to the first aspect of the invention.

In a fourth aspect, the present invention provides processes for producing an unsaturated nitrile which comprise subjecting an alkane, or a mixture of an alkane and an alkene, and ammonia to a vapor phase catalytic oxidation reaction in the presence of a catalyst according to the first aspect of the invention.

The catalyst of the present invention comprises a mixed metal oxide having the empirical formula $$Mo_aV_bM_cX_dO_e$$

wherein M is an element selected from the group consisting of Te, Sb and Nb,
wherein X is an element selected from the group consisting of Sc, Y, La, Re, Ir, Cu, Ag, Au,
Zn, Ga, Si, Ge, As, Pb, S, Se, Sn, Bi, F, Cl, Br and I, and
wherein, when a=1, b=0.01 to 1.0, c=0.01 to 1.0, d=0 to 1 and e is dependent on the oxidation state of the other elements;
with the proviso that, when d=0, M is selected fom the group consisting of Nb and Te, and
with the further proviso that, when d=0 and M=Te, $0.01 \leq b < 0.50$ or $0.17 \leq c < 1.0$.

Preferably, in the case where d>0, when a=1, b=0.1 to 0.6, c=0.1 to 0.5 and d=0.0001 to 0.5; more preferably, b=0.3 to 0.6, c=0.15 to 0.5 and d=0.001 to 0.1. The value of e, i.e. the amount of oxygen present, is dependent on the oxidation state of the other elements in the catalyst.

A catalyst of the aforementioned composition may be prepared by any suitable technique.

For example, the catalyst may be prepared by the "dry up" method. In the "dry up" method:
compounds of elements Mo, V, M and X and at least one solvent are admixed to form an admixture,
wherein M is an element selected from the group consisting of Te, Sb and Nb, X is an element selected from the group consisting of Sc, Y, La, Re, Ir, Cu, Ag, Au, Zn, Ga,
Si, Ge, As, Pb, S, Se, Sn, Bi, F, Cl, Br and I, wherein Mo, V, M and X are present in such amounts that the atomic ratio of Mo:V:M:X is a:b:c:d, and wherein, when a=1, b=0.01 to 1.0, c=0.01 to 1.0, d=0.01 to 1.0, with the proviso that, when d=0, M is selected from the group consisting of Nb and Te, and with the further proviso that, when d=0 and M=Te, $0.01 \leq b < 0.50$ or $0.17 \leq c < 1.0$;

removing the at least one solvent from said admixture to form a catalyst precursor; and calcining the catalyst precursor to obtain said catalyst.

Suitable solvents include water; alcohols including, but not limited to, methanol, ethanol, propanol, and diols, etc.; as well as other polar solvents known in the art. Generally, water is preferred. The water is any water suitable for use in chemical syntheses including, without limitation, distilled water and de-ionized water. The amount of water present is preferably an amount sufficient to keep the elements substantially in solution long enough to avoid or minimize compositional and/or phase segregation during the preparation steps. Accordingly, the amount of water will vary according to the amounts and solubilities of the materials combined. However, as stated above, the amount of water is preferably sufficient to ensure an aqueous solution is formed, at the time of mixing.

The solvent is removed from the admixture by any suitable method, known in the art, to form a catalyst precursor. Such methods include, without limitation, vacuum drying, freeze drying, spray drying, rotary evaporation and air drying.

For example, in the case of water being the solvent: Vacuum drying is generally performed at pressures ranging from 10 mmHg to 500 mmHg. Freeze drying typically entails freezing the solution, using, for instance, liquid nitrogen, and drying the frozen solution under vacuum. Spray drying is generally performed under an inert atmosphere such as nitrogen or argon, with an inlet temperature ranging from 125° C. to 200° C. and an outlet temperature ranging from 75° C. to 150° C. Rotary evaporation is generally performed at a bath temperature of from 25° C. to 90° C. and at a pressure of from 10 mmHg to 760 mmHg, preferably at a bath temperature of from 40° C. to 90° C. and at a pressure of from 10 mmHg to 350 mmHg, more preferably at a bath temperature of from 40° C. to 60° C. and at a pressure of from 10 mmHg to 40 mmHg. Air drying may be effected at temperatures ranging from 25° C. to 90° C. Rotary evaporation or air drying are generally preferred.

Once obtained, the catalyst precursor is calcined. The calcination may be conducted in an oxygen-containing atmosphere or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 650° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In one mode of operation, the catalyst precursor is calcined in two stages, i.e. the catalyst precursor is heated to a first temperature in an oxidizing atmosphere and, then, the so-treated catalyst precursor is heated from the first temperature to a second temperature in a non-oxidizing atmosphere. Typically, in the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a preferred mode of operation, the catalyst precursor in the first stage is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

In a particularly preferred mode of operation, the catalyst precursor in the first stage of calcination is placed in a desired flowing oxidizing atmosphere at room temperature and then raised to the first stage calcination temperature, at a rate of from 1° C./min to 20° C./min, preferably 2°/min to 10° C./min. It is then held at the first stage calcination temperature, in the desired flowing oxidizing atmosphere, for the desired first stage calcination time. After the desired first stage calcination time has passed, the atmosphere is replaced with a desired flowing non-oxidizing atmosphere, preferably while maintaining the temperature at the first stage calcination temperature; the temperature is then raised to the desired second stage calcination temperature at a rate of from 1° C./min to 20° C./min, preferably 2° C./min to 10° C./min. It is then held at the second stage calcination temperature, in the desired flowing non-oxidizing atmosphere, for the desired second stage calcination time.

With calcination, a catalyst is formed having the formula $Mo_aV_bM_cX_dO_e$ wherein M. X, a, b, c, d and e are as previously defined.

Preferably, in a second aspect of the present invention, the catalyst is formed by a "hydrothermal" technique. In this "hydrothermal" technique:

compounds of elements Mo, V, M and X, as needed, and a solvent comprising water are mixed to form a first admixture containing at least 2 but less than all of said elements Mo, V, M and X;

the first admixture is heated at a temperature of from 80° C. to 150° C. for from 5 minutes to 48 hours;

then, compounds of elements Mo, V, M and X, as needed, are mixed with the first admixture to form a second admixture containing elements Mo, V, M and X, in the respective atomic proportions a, b, c and d, wherein, when a=1, b=0.01 to 1.0, c=0.01 to 1.0 and d=0 to 1;

the second admixture is heated at a temperature of from 50° C. to 300° C. for from 1 hour to several weeks, in a closed vessel under pressure; and insoluble material is recovered from the closed vessel to obtain a catalyst.

Optionally, albeit preferably, the recovered insoluble material is calcined.

In particular, compounds of elements Mo, V, M and X and a solvent comprising water are mixed to form a first admixture. This first admixture contains at least 2, but less than all, of the elements Mo, V, M and X needed to make the desired catalyst composition, wherein M is an element selected from the group consisting of Te, Sb and Nb, X is an element selected from the group consisting of Sc, Y, La, Re, Ir, Cu, Ag, Au, Zn, Ga, Si, Ge, As, Pb, S, Se, Sn, Bi, F, Cl, Br and I, wherein Mo, V, M and X are present in such amounts that the atomic ratio of Mo:V:M:X is a:b:c:d, and wherein, when a=1, b=0.01 to 1.0, c=0.01 to 1.0, d=0.01 to 1.0, with the proviso that, when d=0, M is selected from the group consisting of Nb and Te, and with the further proviso that, when d=0 and M=Te, $0.01 \leq b < 0.50$ or $0.17 < c \leq .1$. In the case of a catalyst containing the elements Mo, V, M and X (d>0), it is preferred to mix compounds of the elements Mo, M and X, compounds of the elements Mo and M or compounds of the elements V and M to form the first admixture. In the case of a catalyst containing the elements Mo, V and M (d=0), it is preferred to mix compound of the elements Mo and M or compounds of the elements V and M to form the first admixture. In either case, it is preferable to utilize the components of the first admixture in the atomic proportions of the elements present in the final catalyst.

The so-formed first admixture may be held at a temperature of 25° C. to 200° C., preferably 50° C. to 175° C., most preferably 75° C. to 150° C., for from 5 minutes to 48 hours, preferably 5 minutes to 10 hours, most preferably 5 minutes to 5 hours. Any solvent or any portion of the solvent that evaporates from the admixture during this treatment may be condensed and returned to the admixture, if so desired, in order to maintain a liquid phase. Alternatively, this treatment of the first admixture may be carried out in a closed container.

Subsequent to the aforementioned treatment of the first admixture, the first admixture is mixed with compounds of the elements Mo, V, M and X, as needed, to form a second admixture containing elements Mo, V, M and X, in the respective atomic proportions a, b, c and d, wherein, when a=1, b=0.01 to 1.0, c=0.01 to 1.0 and d=0 to 1. Preferably, only compounds of elements missing from the first admixture are added in this mixing procedure.

The second admixture is then held at a temperature of 50° C. to 300° C., preferably 100° C. to 250° C., most preferably 150° C. to 200° C., for from 1 hour to several weeks, preferably 2 hours to 7 days, most preferably 5 to 72 hours, in a closed vessel. The closed vessel may be under pressure. The pressure may be the autogenous pressure of the enclosed materials at the particular temperature utilized or it can be an applied pressure, such as could be obtained by feeding a pressurized gaseous atmosphere to the closed vessel. In either case, a gas space over the enclosed admixture may comprise an oxidizing atmosphere such as air, oxygen enriched air or oxygen; a reducing atmosphere such as hydrogen; an inert atmosphere such as nitrogen, argon, helium or mixtures thereof; or mixtures thereof. Moreover, the gas space over the enclosed admixture may be charged with low levels of catalyst promoters such as $NO_x$ compounds, $SO_x$ compounds, gaseous halides or halogens.

After the aforementioned treatment, insoluble material is recovered from the closed vessel. This insoluble material is a very active catalyst, but the selectivity for the desired reaction product, e.g., acrylic acid, is generally poor. When the recovered insoluble material is subjected to calcination, the activity is decreased but the selectivity for the desired reaction product, e.g., acrylic acid, is increased.

In the "hydrothermal" technique, water is preferably used as the solvent in the catalyst preparation. The water is any water suitable for use in chemical syntheses including, without limitation, distilled water and de-ionized water. However, the solvent utilized may further comprise polar solvents such as, for example, water-miscible alcohols, diols, glycols, polyols, ethers, carboxylates, nitrites and amides. The amount of solvent utilized is not critical.

Preferably, the vessel utilized for hydrothermal treatment is formed of a material inert to the hydrothermal reaction or is lined with a material inert to the hydrothermal reaction, e.g., polytetrafluoroethylene (PTFE).

After hydrothermal treatment, insoluble material is recovered from the treating vessel. The insoluble material may be recovered by any conventional method, e.g., centrifugation or filtration. Preferably the hydrothermally treated material is cooled prior to recovery of the insoluble material. If desired, the insoluble material may be washed one or more times with water.

The recovered insoluble material may then be dried by any suitable method known in the art. Such methods include, without limitation, vacuum drying, freeze drying and air drying.

For example, in order to remove any residual water: Vacuum drying is generally performed at pressures ranging from 10 mmHg to 500 mmHg, with or without the application of heat. Freeze drying typically entails freezing the recovered material, using, for instance, liquid nitrogen, and drying the frozen material under vacuum. Air drying may be effected at temperatures ranging from 25° C. to 90° C.

Calcination of the recovered insoluble material may be conducted in an oxidizing atmosphere, e.g., in air, oxygen-enriched air or oxygen, or in the substantial absence of oxygen, e.g., in an inert atmosphere or in vacuo. The inert atmosphere may be any material which is substantially inert, i.e., does not react or interact with, the catalyst precursor. Suitable examples include, without limitation, nitrogen, argon, xenon, helium or mixtures thereof. Preferably, the inert atmosphere is argon or nitrogen. The inert atmosphere may flow over the surface of the catalyst precursor or may not flow thereover (a static environment). When the inert atmosphere does flow over the surface of the catalyst precursor, the flow rate can vary over a wide range, e.g., at a space velocity of from 1 to 500 $hr^{-1}$.

The calcination is usually performed at a temperature of from 350° C. to 850° C., preferably from 400° C. to 700° C., more preferably from 500° C. to 640° C. The calcination is performed for an amount of time suitable to form the aforementioned catalyst. Typically, the calcination is performed for from 0.5 to 30 hours, preferably from 1 to 25 hours, more preferably for from 1 to 15 hours, to obtain the desired promoted mixed metal oxide.

In a preferred mode of operation, calcination is conducted in two stages, i.e. the recovered insoluble material is heated to a first temperature in an oxidizing atmosphere and, then, the so-treated recovered insoluble material is heated from the first temperature to a second temperature in a non-oxidizing atmosphere. Typically, in the first stage, the catalyst precursor is calcined in an oxidizing environment (e.g. air) at a temperature of from 200° C. to 400° C., preferably from 275° C. to 325° C. for from 15 minutes to 8 hours, preferably for from 1 to 3 hours. In the second stage, the material from the first stage is calcined in a non-oxidizing environment (e.g., an inert atmosphere) at a temperature of from 500° C. to 750° C., preferably for from 550° C. to 650° C., for 15 minutes to 8 hours, preferably for from 1 to 3 hours. Optionally, a reducing gas, such as, for example, ammonia or hydrogen, may be added during the second stage calcination.

In a particularly preferred mode of operation, in the first stage, the material to be calcined is placed in the desired oxidizing atmosphere at room temperature and then raised to the first stage calcination temperature and held there for the desired first stage calcination time. The atmosphere is then replaced with the desired non-oxidizing atmosphere for the second stage calcination, the temperature is raised to the desired second stage calcination temperature and held there for the desired second stage calcination time.

In an another preferred mode of operation, the insoluble material recovered from the contact mixture is calcined in a non-oxidizing atmosphere, preferably an inert atmosphere. In the case where the promoter element, i.e. the element X is a halogen, such halogen may be added to the aforementioned non-oxidizing atmosphere.

Although any type of heating mechanism, e.g., a furnace, may be utilized during the calcination, it is preferred to conduct the calcination under a flow of the designated gaseous environment. Therefore, it is advantageous to conduct the calcination in a bed with continuous flow of the desired gas(es) through the bed of solid catalyst precursor particles.

The starting materials for the above mixed metal oxide are not particularly limited. A wide range of materials including, for example, oxides, nitrates, halides or oxyhalides, alkoxides, acetylacetonates, and organometallic compounds may be used. For example, ammonium heptamolybdate may be utilized for the source of molybdenum in the catalyst. However, compounds such as $MoO_3$, $MoO_2$, $MoCl_5$, $MoOCl_4$, $Mo(OC_2H_5)_5$, molybdenum acetylacetonate, phosphomolybdic acid and silicomolybdic acid may also be utilized instead of ammonium heptamolybdate. Similarly, vanadyl sulfate ($VOSO_4$) may be utilized for the source of vanadium in the catalyst. However, compounds such as $V_2O_5$, $V_2O_3$, $VOCl_3$, $VCl_4$, $VO(OC_2H_5)_3$, vanadium acetylacetonate and vanadyl acetylacetonate may also be utilized instead of vanadyl sulfate. $TeO_2$ may be utilized for the source of tellurium in the catalyst. However, $TeCl_4$, $Te(OC_2H_5)_5$ and $Te(OCH(CH_3)_2)_4$ may also be utilized instead of $TeO_2$. The niobium source may include ammonium niobium oxalate, $Nb_2O_5$, $NbCl_5$, niobic acid or $Nb(OC_2H_5)_5$ as well as the more conventional niobium oxalate.

With respect to the other elements or compounds thereof that may be utilized to make the improved catalysts of the present invention, no particular restrictions are placed thereon. With this in mind, the following lists are merely illustrative of available sources of some of these elements or the compounds thereof, and are not meant to be limiting hereon.

The gold source may be ammonium tetrachloroaurate, gold bromide, gold chloride, gold cyanide, gold hydroxide, gold iodide, gold oxide, gold trichloride acid or gold sulfide.

The silver source may be silver acetate, silver acetylacetonate, silver benzoate, silver bromide, silver carbonate, silver chloride, silver citrate hydrate, silver fluoride, silver iodide, silver lactate, silver nitrate, solver nitrite, silver oxide, silver phosphate, or a solution of silver in an aqueous inorganic acid, e.g., nitric acid.

The copper source may be copper acetate, copper acetate monohydrate, copper acetate hydrate, copper acetylacetonate, copper bromide, copper carbonate, copper chloride, copper chloride dihydrate, copper fluoride, copper formate hydrate, copper gluconate, copper hydroxide, copper iodide, copper methoxide, copper nitrate hydrate, copper nitrate, copper oxide, copper tartrate hydrate, or a solution of copper in an aqueous inorganic acid, e.g., nitric acid.

The yittrium source may be an yittrium salt, e.g., yittrium nitrate, dissolved in water.

The scandium source may be scandium acetate, scandium bromide hydrate, scandium chloride, scandium chloride hexahydrate, scandium chloride hydrate, scandium fluoride, scandium iodide, scandium isopropoxide, scandium nitrate hydrate, scandium oxalate hydrate, scandium oxide, or a solution of scandium in an aqueous inorganic acid, e.g., nitric acid.

The rhenium source may be ammonium perrhenate, rhenium carbonyl, rhenium chloride, rhenium fluoride, rhenium oxide, rhenium pentacarbonyl bromide, rhenium pentacarbonyl chloride and rhenium sulfide.

The iridium source may be iridium acetylacetonate, iridium bromide hydrate, iridium chloride, iridium chloride hydrochloride hydrate, iridium chloride hydrate, iridium oxide, iridium oxide hydrate, iridium oxoacetate trihydrate or iridium dissolved in an aqueous inorganic acid, e.g., nitric acid.

The zinc source may be zinc acetate, zinc acetylacetonate, zinc acrylate, zinc bis(2,2,6,6-tetramethyl-3,5-heptanedioate), zinc bromide, zinc carbonate hydroxide, zinc chloride, zinc citrate, zinc cyclohexanebutyrate, zinc 3,5-di-tert-butylsalicylate, zinc fluoride, zinc iodide, zinc L-lactate, zinc methacrylate, zinc nitrate, zinc oxide, zinc perchlorate or zinc stearate.

The gallium source may be $Ga_2O$, $GaCl_3$, $GaCl_2$, gallium acetylacetonate, $Ga_2O_3$ or $Ga(NO_3)_3$.

The bromine source may be added as one of the above reagents as a bromide, e.g., as the bromide salt of X (where X is at least one element selected from the group consisting of W, Ta, Ti, Al, Zr, Cr, Mn, Fe, Ru, Co, Rh, Ni, Pt, B, In, As, Ge, Sn, Li, Na, K, Rb, Cs, Fr, Be, Mg, Ca, Sr, Ba, Hf, Pb, P, Pm, Eu, Gd, Dy, Ho, Er, Tm, Yb and Lu), for example, as molybdenum bromide, tellurium tetrabromide or vanadium bromide; or as a solution of bromine in an aqueous inorganic acid, e.g., nitric acid. The bromine source may also be added during the calcination of the recovered insoluble material or, after calcination, as a bromine treatment step. For example, the bromine source may be added to the calcination atmosphere or to the oxidation or ammoxidation reactor feed stream, as, for example, HBr, $Br_2$, ethyl bromide or the like, to achieve a promotional effect with the bromine.

The chlorine source may also be added as one of the above reagents as a chloride, e.g., as the chloride salt of X (where X is at least one element selected from the group consisting of W, Ta, Ti, Al, Zr, Cr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum chloride, tellurium tetrachloride or vanadium chloride. The chlorine source may also be added during the calcination of the recovered insoluble material or, after calcination, as a chlorine treatment step. For example, the chlorine source may be added to the calcination atmosphere or to the oxidation or ammoxidation reactor feed stream, as, for example, HCl, Cl$_2$, ethyl chloride or the like, to achieve a promotional effect with the chloride.

The fluorine source may be added as one of the above reagents as a fluoride, e.g., as the fluoride salt of X (where X is at least one element selected from the group consisting of W, Ta, Ti, Al, Zr, Cr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum fluoride, tellurium fluoride or vanadium fluoride. The fluorine source may also be added during the calcination of the recovered insoluble material or, after calcination, as a fluorine treatment step. For example, the fluorine source may be added to the calcination atmosphere or to the oxidation or ammoxidation reactor feed stream, as, for example, HF, F$_2$, ethyl fluoride or the like, to achieve a promotional effect with the fluoride.

The iodine source may be added as one of the above reagents as a fluoride, e.g., as the fluoride salt of X (where X is at least one element selected from the group consisting of W, Ta, Ti, Al, Zr, Cr, Mn, Fe, Ru, Co, Rh, Ni, Pt, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu), for example, as molybdenum iodide, tellurium iodide or vanadium iodide. The iodine source may also be added during the calcination of the recovered insoluble material or, after calcination, as an iodine treatment step. For example, the iodine source may be added to the calcination atmosphere or to the oxidation or ammoxidation reactor feed stream, as, for example, HI, I$_2$, ethyl iodide or the like, to achieve a promotional effect with the iodide.

The catalyst formed by the aforementioned techniques, exhibits good catalytic activities by itself. However, the mixed metal oxide may be converted to a catalyst having higher activities by grinding.

There is no particular restriction as to the grinding method, and conventional methods may be employed. As a dry grinding method, a method of using a gas stream grinder may, for example, be mentioned wherein coarse particles are permitted to collide with one another in a high speed gas stream for grinding. The grinding may be conducted not only mechanically but also by using a mortar or the like in the case of a small scale operation.

As a wet grinding method wherein grinding is conducted in a wet state by adding water or an organic solvent to the above mixed metal oxide, a conventional method of using a rotary cylinder-type medium mill or a medium-stirring type mill, may be mentioned. The rotary cylinder-type medium mill is a wet mill of the type wherein a container for the object to be ground is rotated, and it includes, for example, a ball mill and a rod mill. The medium-stirring type mill is a wet mill of the type wherein the object to be ground, contained in a container is stirred by a stirring apparatus, and it includes, for example, a rotary screw type mill, and a rotary disc type mill.

The conditions for grinding may suitably be set to meet the nature of the above-mentioned promoted mixed metal oxide, the viscosity, the concentration, etc. of the solvent used in the case of wet grinding, or the optimum conditions of the grinding apparatus.

Further, in some cases, it is possible to further improve the catalytic activities by further adding a solvent to the ground catalyst precursor to form a solution or slurry, followed by drying again. There is no particular restriction as to the concentration of the solution or slurry, and it is usual to adjust the solution or slurry so that the total amount of the starting material compounds for the ground catalyst precursor is from 10 to 60 wt %. Then, this solution or slurry is dried by a method such as spray drying, freeze drying, evaporation to dryness or vacuum drying, preferably by the spray drying method. Further, similar drying may be conducted also in the case where wet grinding is conducted.

The oxide obtained by the above-mentioned method may be used as a final catalyst, but it may further be subjected to heat treatment usually at a temperature of from 200° to 700° C. for from 0.1 to 10 hours.

The mixed metal oxide thus obtained may be used by itself as a solid catalyst, but may be formed into a catalyst together with a suitable carrier such as silica, alumina, titania, aluminosilicate, diatomaceous earth or zirconia. Further, it may be molded into a suitable shape and particle size depending upon the scale or system of the reactor.

In its third aspect, the present invention provides a process for producing an unsaturated carboxylic acid, which comprises subjecting an alkane, or a mixture of an alkane and an alkene, to a vapor phase catalytic oxidation reaction in the presence of a catalyst according to the first aspect of the invention.

In the production of such an unsaturated carboxylic acid, it is preferred to employ a starting material gas which contains steam. In such a case, as a starting material gas to be supplied to the reaction system, a gas mixture comprising a steam-containing alkane, or a steam-containing mixture of alkane and alkene, and an oxygen-containing gas, is usually used. However, the steam-containing alkane, or the steam-containing mixture of alkane and alkene, and the oxygen-containing gas may be alternately supplied to the reaction system. The steam to be employed may be present in the form of steam gas in the reaction system, and the manner of its introduction is not particularly limited.

In regard to the use of a halogen as an element of the catalyst of the present invention, it is possible to add a gaseous halogen source as previously identified to the gas feed to the reaction.

Further, as a diluting gas, an inert gas such as nitrogen, argon or helium may be supplied. The molar ratio (alkane or mixture of alkane and alkene):(oxygen):(diluting gas):(H$_2$O) in the starting material gas is preferably (1):(0.1 to 10):(0 to 20):(0.2 to 70), more preferably (1):(1 to 5.0):(0 to 10):(5 to 40).

When steam is supplied together with the alkane, or the mixture of alkane and alkene, as starting material gas, the selectivity for an unsaturated carboxylic acid is distinctly improved, and the unsaturated carboxylic acid can be obtained from the alkane, or mixture of alkane and alkene, in good yield simply by contacting in one stage. However, the conventional technique utilizes a diluting gas such as nitrogen, argon or helium for the purpose of diluting the starting material. As such a diluting gas, to adjust the space velocity, the oxygen partial pressure and the steam partial pressure, an inert gas such as nitrogen, argon or helium may be used together with the steam.

As the starting material alkane it is preferred to employ a C$_{3-8}$alkane, particularly propane, isobutane or n-butane; more preferably, propane or isobutane; most preferably, propane. According to the present invention, from such an alkane, an unsaturated carboxylic acid such as an α,β-unsaturated carboxylic acid can be obtained in good yield. For example, when propane or isobutane is used as the starting material alkane, acrylic acid or methacrylic acid will be obtained, respectively, in good yield.

In the present invention, as the starting material mixture of alkane and alkene, it is possible to employ a mixture of C$_{3-8}$alkane and C$_{3-8}$alkene, particularly propane and propene, isobutane and isobutene or n-butane and n-butene. As the starting material mixture of alkane and alkene, propane and propene or isobutane and isobutene are more preferred. Most preferred is a mixture of propane and propene. According to the present invention, from such a mixture of an alkane and an alkene, an unsaturated carboxylic acid such as an α,β-unsaturated carboxylic acid can be obtained in good yield. For example, when propane and propene or isobutane and isobutene are used as the starting material mixture of alkane and alkene, acrylic acid or methacrylic acid will be obtained, respectively, in good yield. Preferably, in the mixture of alkane and alkene, the alkene is present in an amount of at least 0.5% by weight, more preferably at least 1.0% by weight to 95% by weight; most preferably, 3% by weight to 90% by weight.

As an alternative, an alkanol, such as isobutanol, which will dehydrate under the reaction conditions to form its corresponding alkene, i.e. isobutene, may also be used as a feed to the present process or in conjunction with the previously mentioned feed streams.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the oxidation reaction of the present invention is not clearly understood, but the oxidation reaction is carried out by oxygen atoms present in the above promoted mixed metal oxide or by molecular oxygen present in the feed gas. To incorporate molecular oxygen into the feed gas, such molecular oxygen may be pure oxygen gas. However, it is usually more economical to use an oxygen-containing gas such as air, since purity is not particularly required.

It is also possible to use only an alkane, or a mixture of alkane and alkene, substantially in the absence of molecular oxygen for the vapor phase catalytic reaction. In such a case, it is preferred to adopt a method wherein a part of the catalyst is appropriately withdrawn from the reaction zone from time to time, then sent to an oxidation regenerator, regenerated and then returned to the reaction zone for reuse. As the regeneration method of the catalyst, a method may, for example, be mentioned which comprises contacting an oxidative gas such as oxygen, air or nitrogen monoxide with the catalyst in the regenerator usually at a temperature of from 300° to 600° C.

This aspect of the present invention will be described in further detail with respect to a case where propane is used as the starting material alkane and air is used as the oxygen source. The reaction system may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, preferably from 0.2 to 18 moles per mole of propane, whereby high selectivity for acrylic acid can be obtained. This reaction can be conducted usually under atmospheric pressure, but may be conducted under a slightly elevated pressure or slightly reduced pressure. With respect to other alkanes such as isobutane, or to mixtures of alkanes and alkenes such as propane and propene, the composition of the feed gas may be selected in accordance with the conditions for propane.

Typical reaction conditions for the oxidation of propane or isobutane to acrylic acid or methacrylic acid may be utilized in the practice of the present invention. The process may be practiced in a single pass mode (only fresh feed is fed to the reactor) or in a recycle mode (at least a portion of the reactor effluent is returned to the reactor). General conditions for the process of the present invention are as follows: the reaction temperature can vary from 200° C. to 700° C., but is usually in the range of from 200° C. to 550° C., more preferably 250° C. to 480° C., most preferably 300° C. to 400° C.; the gas space velocity, SV, in the vapor phase reaction is usually within a range of from 100 to 10,000 $hr^{-1}$, preferably 300 to 6,000 $hr^{-1}$, more preferably 300 to 2,000 $hr^{-1}$; the average contact time with the catalyst can be from 0.01 to 10 seconds or more, but is usually in the range of from 0.1 to 10 seconds, preferably from 2 to 6 seconds; the pressure in the reaction zone usually ranges from 0 to 75 psig, but is preferably no more than 50 psig. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Of course, in the oxidation reaction of the present invention, it is important that the hydrocarbon and oxygen concentrations in the feed gases be maintained at the appropriate levels to minimize or avoid entering a flammable regime within the reaction zone or especially at the outlet of the reactor zone. Generally, it is preferred that the outlet oxygen levels be low to both minimize after-burning and, particularly, in the recycle mode of operation, to minimize the amount of oxygen in the recycled gaseous effluent stream. In addition, operation of the reaction at a low temperature (below 450° C.) is extremely attractive because after-burning becomes less of a problem which enables the attainment of higher selectivity to the desired products. The catalyst of the present invention operates more efficiently at the lower temperature range set forth above, significantly reducing the formation of acetic acid and carbon oxides, and increasing selectivity to acrylic acid. As a diluting gas to adjust the space velocity and the oxygen partial pressure, an inert gas such as nitrogen, argon or helium may be employed.

When the oxidation reaction of propane, and especially the oxidation reaction of propane and propene, is conducted by the method of the present invention, carbon monoxide, carbon dioxide, acetic acid, etc. may be produced as by-products, in addition to acrylic acid. Further, in the method of the present invention, an unsaturated aldehyde may sometimes be formed depending upon the reaction conditions. For example, when propane is present in the starting material mixture, acrolein may be formed; and when isobutane is present in the starting material mixture, methacrolein may be formed. In such a case, such an unsaturated aldehyde can be converted to the desired unsaturated carboxylic acid by subjecting it again to the vapor phase catalytic oxidation with the promoted mixed metal oxide-containing catalyst of the present invention or by subjecting it to a vapor phase catalytic oxidation reaction with a conventional oxidation reaction catalyst for an unsaturated aldehyde.

In its fourth aspect, the present invention provides a process for producing an unsaturated nitrile, which comprises subjecting an alkane, or a mixture of an alkane and an alkene, to a vapor phase catalytic oxidation reaction with ammonia in the presence of a catalyst according to the first aspect of the invention.

In regard to the use of a halogen as an element of the catalyst of the present invention, it is possible to add a gaseous halogen source as previously identified to the gas feed to the reaction.

In the production of such an unsaturated nitrile, as the starting material alkane, it is preferred to employ a $C_{3-8}$ alkane such as propane, butane, isobutane, pentane, hexane and heptane. However, in view of the industrial application of nitrites to be produced, it is preferred to employ a lower alkane having 3 or 4 carbon atoms, particularly propane and isobutane.

Similarly, as the starting material mixture of alkane and alkene, it is possible to employ a mixture of $C_{3-8}$ alkane and $C_{3-8}$ alkene such as propane and propene, butane and butene, isobutane and isobutene, pentane and pentene, hexane and hexene, and heptane and heptene. However, in view of the industrial application of nitrites to be produced, it is more preferred to employ a mixture of a lower alkane having 3 or 4 carbon atoms and a lower alkene having 3 or 4 carbon atoms, particularly propane and propene or isobutane and isobutene. Preferably, in the mixture of alkane and alkene, the alkene is present in an amount of at least 0.5% by weight, more preferably at least 1.0% by weight to 95% by weight, most preferably 3% by weight to 90% by weight.

The purity of the starting material alkane is not particularly limited, and an alkane containing a lower alkane such as methane or ethane, air or carbon dioxide, as impurities, may be used without any particular problem. Further, the starting material alkane may be a mixture of various alkanes. Similarly, the purity of the starting material mixture of alkane and alkene is not particularly limited, and a mixture of alkane and alkene containing a lower alkene such as ethene, a lower alkane such as methane or ethane, air or carbon dioxide, as impurities, may be used without any particular problem. Further, the starting material mixture of alkane and alkene may be a mixture of various alkanes and alkenes.

There is no limitation on the source of the alkene. It may be purchased, per se, or in admixture with an alkane and/or other impurities. Alternatively, it can be obtained as a by-product of alkane oxidation. Similarly, there is no limitation on the source of the alkane. It may be purchased, per se, or in admixture with an alkene and/or other impurities. Moreover, the alkane, regardless of source, and the alkene, regardless of source, may be blended as desired.

The detailed mechanism of the ammoxidation reaction of this aspect of the present invention is not clearly understood. However, the oxidation reaction is conducted by the oxygen atoms present in the above promoted mixed metal oxide or by the molecular oxygen in the feed gas. When molecular oxygen is incorporated in the feed gas, the oxygen may be pure oxygen gas. However, since high purity is not required, it is usually economical to use an oxygen-containing gas such as air.

As the feed gas, it is possible to use a gas mixture comprising an alkane, or a mixture of an alkane and an alkene, ammonia and an oxygen-containing gas, However, a gas mixture comprising an alkane or a mixture of an alkane and an alkene and ammonia, and an oxygen-containing gas may be supplied alternately.

When the gas phase catalytic reaction is conducted using an alkane, or a mixture of an alkane and an alkene, and ammonia substantially free from molecular oxygen, as the feed gas, it is advisable to employ a method wherein a part of the catalyst is periodically withdrawn and sent to an oxidation regenerator for regeneration, and the regenerated catalyst is returned to the reaction zone. As a method for regenerating the catalyst, a method may be mentioned wherein an oxidizing gas such as oxygen, air or nitrogen monoxide is permitted to flow through the catalyst in the regenerator usually at a temperature of from 300° C. to 600° C.

This aspect of the present invention will be described in further detail with respect to a case where propane is used as the starting material alkane and air is used as the oxygen source. The proportion of air to be supplied for the reaction is important with respect to the selectivity for the resulting acrylonitrile. Namely, high selectivity for acrylonitrile is obtained when air is supplied within a range of at most 25 moles, particularly 1 to 15 moles, per mole of the propane. The proportion of ammonia to be supplied for the reaction is preferably within a range of from 0.2 to 5 moles, particularly from 0.5 to 3 moles, per mole of propane. This reaction may usually be conducted under atmospheric pressure, but may be conducted under a slightly increased pressure or a slightly reduced pressure. With respect to other alkanes such as isobutane, or to mixtures of alkanes and alkenes such as propane and propene, the composition of the feed gas may be selected in accordance with the conditions for propane.

The process of this aspect of the present invention may be conducted at a temperature of, for example, from 250° C. to 480° C. More preferably, the temperature is from 300° C. to 400° C. The gas space velocity, SV, in the gas phase reaction is usually within the range of from 100 to 10,000 $hr^{-1}$, preferably from 300 to 6,000 $hr^{-1}$, more preferably from 300 to 2,000 $hr^{-1}$. As a diluent gas, for adjusting the space velocity and the oxygen partial pressure, an inert gas such as nitrogen, argon or helium can be employed. When ammoxidation of propane is conducted by the method of the present invention, in addition to acrylonitrile, carbon monoxide, carbon dioxide, acetonitrile, hydrocyanic acid and acrolein may form as by-products.

EXAMPLES

Catalyst Preparation

Comparative Example 1

To a 45 mL Parr Acid Digestion Bomb with an inner tube made of PTFE, 0.53 g of tellurium dioxide (Aldrich) and 20 mL of aqueous solution of ammonium heptamolybdate tetrahydrate (Aldrich, 1.0 M in Mo) were added, and then 10 mL of aqueous solution of vanadyl sulfate hydrate (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of MoV$_{0.5}$Te$_{017}$Ox. The catalyst thus obtained was pressed in a mold and then broken and sieved to 10–20 mesh granules for reactor evaluation.

Example 1

To a 45 mL Parr Acid Digestion Bomb with an inner tube made of PTFE, 0.53 g of tellurium dioxide (Aldrich), 5 mL of gallium(III) nitrate hydrate in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Ga$_{0.025}$MoV$_{0.5}$Te$_{0.17}$O$_x$. The catalyst thus obtained was pressed in a mold and then broken and sieved to 10–20 mesh granules for reactor evaluation.

Example 2

To a 45 mL Parr Acid Digestion Bomb with an inner tube made of PTFE, 0.53 g of tellurium dioxide (Aldrich), 1 mL of VBr$_3$ in water (Aldrich, 0.1 M in Br) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Br$_{0.005}$MoV$_{0.5}$Te$_{0.17}$O$_x$. The catalyst thus obtained was pressed in a mold and then broken and sieved to 10–20 mesh granules for reactor evaluation.

Example 3

To a 45 mL Parr Acid Digestion Bomb with an inner tube made of PTFE, 0.53 g of tellurium dioxide (Aldrich), 1 mL of VF$_3$ in water (Aldrich, 0.1 M in F) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of F$_{0.005}$MoV$_{0.5}$Te$_{0.17}$O$_x$. The catalyst thus obtained was pressed in a mold and then broken and sieved to 10–20 mesh granules for reactor evaluation.

Example 4

To a 45 mL Parr Acid Digestion Bomb with an inner tube made of PTFE, 0.53 g of tellurium dioxide (Aldrich), 1 mL of Bi(NO$_3$)$_3$.5H$_2$O in 5% nitric acid (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Bi$_{0.005}$MoV$_{0.5}$Te$_{0.17}$O$_x$. The catalyst thus obtained was pressed in a mold and then broken and sieved to 10–20 mesh granules for reactor evaluation.

Example 5

To a 45 mL Parr Acid Digestion Bomb with an inner tube made of PTFE, 0.53 g of tellurium dioxide (Aldrich), 1 mL of VI$_3$ in water (Aldrich, 0.1 M in I) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of I$_{0.005}$MoV$_{0.5}$Te$_{0.17}$O$_x$. The catalyst thus obtained was pressed in a mold and then broken and sieved to 10–20 mesh granules for reactor evaluation.

Example 6

To a 45 mL Parr Acid Digestion Bomb with an inner tube made of PTFE, 0.53 g of tellurium dioxide (Aldrich), 0.01 g of GeO$_2$ (Aldrich) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Ge$_{0.005}$MoV$_{0.5}$Te$_{0.17}$O$_x$. The catalyst thus obtained was pressed in a mold and then broken and sieved to 10–20 mesh granules for reactor evaluation.

Example 7

To a 45 mL Parr Acid Digestion Bomb with an inner tube made of PTFE, 0.53 g of tellurium dioxide (Aldrich), 5 mL of La(NO$_3$)$_3$.6H$_2$O in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of La$_{0.025}$MoV$_{0.5}$Te$_{0.17}$O$_x$. The catalyst thus obtained was pressed in a mold and then broken and sieved to 10–20 mesh granules for reactor evaluation.

Example 8

To a 45 mL Parr Acid Digestion Bomb with an inner tube made of PTFE, 0.53 g of tellurium dioxide (Aldrich), 1 mL of Y(NO$_3$)$_3$.6H$_2$O in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Y$_{0.005}$MoV$_{0.5}$Te$_{0.17}$O$_x$. The catalyst thus obtained was pressed in a mold and then broken and sieved to 10–20 mesh granules for reactor evaluation.

Example 9

To a 45 mL Parr Acid Digestion Bomb with an inner tube made of PTFE, 1.06 g of tellurium dioxide (Aldrich), 1 mL of Y(NO$_3$)$_3$.6H$_2$O in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Y$_{0.005}$MoV$_{0.5}$Te$_{0.33}$O$_x$. The catalyst thus obtained was pressed in a mold and then broken and sieved to 10–20 mesh granules for reactor evaluation.

Example 10

To a 45 mL Parr Acid Digestion Bomb with an inner tube made of PTFE, 0.53 g of tellurium dioxide (Aldrich), 5 mL of AgNO$_3$ in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Ag$_{0.025}$MoV$_{0.5}$Te$_{0.17}$O$_x$. The catalyst thus obtained was pressed in a mold and then broken and sieved to 10–20 mesh granules for reactor evaluation.

Example 11

To a 45 mL Parr Acid Digestion Bomb with an inner tube made of PTFE, 0.53 g of tellurium dioxide (Aldrich), 1 mL of Zn(NO$_3$)$_2$.6H$_2$O in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 ML), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Zn$_{0.005}$MoV$_{0.5}$Te$_{0.17}$O$_x$. The catalyst thus obtained was pressed in a mold and then broken and sieved to 10–20 mesh granules for reactor evaluation.

Example 12

To a 45 mL Parr Acid Digestion Bomb with an inner tube made of PTFE, 0.53 g of tellurium dioxide (Aldrich), 0.2 mL of Au(OH)$_3$ in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of Au$_{0.001}$MoV$_{0.5}$Te$_{0.17}$O$_x$. The catalyst thus obtained was pressed in a mold and then broken and sieved to 10–20 mesh granules for reactor evaluation.

Example 13

To a 45 mL Parr Acid Digestion Bomb with an inner tube made of PTFE, 0.53 g of tellurium dioxide (Aldrich), 1 mL of H$_5$As$_3$O$_{10}$ in water (Aldrich, 0.1 M in As) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of $As_{0.005}MoV_{0.5}Te_{0.17}O_x$. The catalyst thus obtained was pressed in a mold and then broken and sieved to 10–20 mesh granules for reactor evaluation.

Example 14

To a 45 mL Parr Acid Digestion Bomb with an inner tube made of PTFE, 0.53 g of tellurium dioxide (Aldrich), 1 mL of $Pb(NO_3)_2$ in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of $Pb_{0.005}MoV_{0.5}Te_{0.17}O_x$. The catalyst thus obtained was pressed in a mold and then broken and sieved to 10–20 mesh granules for reactor evaluation.

Example 15

To a 45 mL Parr Acid Digestion Bomb with an inner tube made of PTFE, 0.53 g of tellurium dioxide (Aldrich), 0.2 mL of $SeO_2$ in water (Aldrich, 0.1 M) and 20 mL of ammonium heptamolybdate tetrahydrate in water (Aldrich, 1.0 M in Mo) were added, and then 10 mL of vanadyl sulfate hydrate in water (Aldrich, 1.0 M in V) was added dropwise at ambient temperature with stirring. The mixed suspension was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of $Se_{0.001}MoV_{0.5}Te_{0.17}O_x$. The catalyst thus obtained was pressed in a mold and then broken and sieved to 10–20 mesh granules for reactor evaluation.

Example 16

To a 100 mL Pyrex beaker, 1.06 g of tellurium dioxide (Aldrich) and 20 mL of ammonium heptamolybdate tetrahydrate in water (Aldrich, 1.0 M in Mo) were added. The mixture was heated on a hot plate at 80–100° C. for 5 min., then 6.7 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 300° C. at 3° C./min and held at 300° C. for 1 hour in air and 1 hour in Ar, then heated in Ar from 300 to 575° C. at 10° C./min and held at 575° C. for 2 hours. The final catalyst had a nominal composition of $MoV_{0.33}Te_{0.33}O_x$. The catalyst thus obtained was pressed in a mold and then broken and sieved to 10–20 mesh granules for reactor evaluation.

Example 17

To a 45 mL Parr Acid Digestion Bomb with an inner tube made of PTFE, 1.06 g of tellurium dioxide (Aldrich) and 20 mL of ammonium heptamolybdate tetrahydrate in water (Aldrich, 1.0 M in Mo) were added. The mixture was first hydrothermally treated at 150° C. for 1 hr, and then 6.7 mL of vanadyl sulfate hydrate in water (Aldrich, 1.0 M in V) were added to the bomb at 60° C. with stirring. The bomb contents were hydrothermally treated at 175° C. for 60 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 575° C. at 2° C./min and held at 575° C. for 2 hours. The final catalyst had a nominal composition of $MoV_{0.33}Te_{0.33}O_x$. The catalyst thus obtained was pressed in a mold and then broken and sieved to 10–20 mesh granules for reactor evaluation.

Example 18

To a 45 mL Parr Acid Digestion Bomb with an inner tube made of PTFE, 1.06 g of tellurium dioxide (Aldrich) and 20 mL of ammonium heptamolybdate tetrahydrate in water (Aldrich, 1.0 M in Mo) were added. The mixture was first hydrothermally treated at 100° C. for 1 hr, and then 10 mL of vanadyl sulfate hydrate in water (Aldrich, 1.0 M in V) were added to the bomb at 60° C. with stirring. The bomb contents were hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 300° C. at 3° C./min and held at 300° C. for 1 hour in air and 1 hour in Ar, then heated in Ar from 300 to 575° C. at 10° C./min and held at 575° C. for 2 hours. The final catalyst had a nominal composition of $MoV_{0.5}Te_{0.33}O_x$. The catalyst thus obtained was pressed in a mold and then broken and sieved to 10–20 mesh granules for reactor evaluation.

Example 19

To a 45 mL Parr Acid Digestion Bomb with an inner tube made of PTFE, 1.59 g of tellurium dioxide (Aldrich) and 20 mL of ammonium heptamolybdate tetrahydrate in water (Aldrich, 1.0 M in Mo) were added. The mixture was first hydrothermally treated at 100° C. for 1 hr, and then 10 mL of vanadyl sulfate hydrate in water (Aldrich, 1.0 M in V) were added to the bomb at 60° C. with stirring. The bomb contents were hydrothermally treated at 175° C. for 60 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 575° C. at 2° C./min and held at 575° C. for 2 hours. The final catalyst had a nominal composition of $MoV_{0.5}Te_{0.5}O_x$. The catalyst thus obtained was pressed in a mold and then broken and sieved to 10–20 mesh granules for reactor evaluation.

Example 20

To a 45 mL Parr Acid Digestion Bomb with an inner tube made of PTFE, 1.03 g of tellurium dioxide (Aldrich), 20 mL of ammonium heptamolybdate tetrahydrate in water (Aldrich, 1.0 M in Mo) and 1 mL of aqueous $MoCl_5$ (Aldrich, 0.1 M in Cl) were added. The mixture was first hydrothermally treated at 100° C. for 1 hr, and then 10 mL of vanadyl sulfate hydrate in water (Aldrich, 1.0 M in V) were added to the bomb at 60° C. with stirring. The bomb contents were hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 300° C. at 3° C./min and held at 300° C. for 1 hour in air and 1 hour in Ar, then heated in Ar from 300 to 575° C. at 10° C./min and held at 575° C. for 2 hours. The final catalyst had a nominal composition of $Cl_{0.025}MoV_{0.05}Te_{0.33}O_x$. The catalyst thus obtained was pressed in a mold and then broken and sieved to 10–20 mesh granules for reactor evaluation.

Example 21

To a 45 mL Parr Acid Digestion Bomb with an inner tube made of PTFE, 1.03 g of tellurium dioxide (Aldrich), 20 mL of ammonium heptamolybdate tetrahydrate in water (Aldrich, 1.0 M in Mo) and 1 mL of $H_5As_3O_{10}$ in water (Aldrich, 0.1 M in As) were added. The mixture was first hydrothermally treated at 80° C. for 1 hr, and then 10 mL of vanadyl sulfate hydrate in water (Aldrich, 1.0 M in V) were added to the bomb at 60° C. with stirring. The bomb contents were hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 600° C. at 2° C./min and held at 600° C. for 2 hours. The final catalyst had a nominal composition of $As_{0.025}MoV_{0.5}Te_{0.33}O_x$. The catalyst thus obtained was pressed in a mold and then broken and sieved to 10–20 mesh granules for reactor evaluation.

Example 22

To a 100 mL Pyrex beaker, 1.06 g of tellurium dioxide (Aldrich), 20 mL of ammonium heptamolybdate tetrahydrate in water (Aldrich, 1.0 M in Mo) and 1 mL of $H_5As_3O_{10}$ in water (Aldrich, 0.1 M in As) were added. The mixture was heated on a hot plate at 80–100° C. for 5 min., then 10 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 575° C. at 2° C./min and held at 575° C. for 2 hours. The final catalyst had a nominal composition of $As_{0.025}MoV_{0.5}Te_{0.33}O_x$. The catalyst thus obtained was pressed in a mold and then broken and sieved to 10–20 mesh granules for reactor evaluation.

Example 23

To a 100 mL Pyrex beaker, 1.06 g of tellurium dioxide (Aldrich), 20 mL of ammonium heptamolybdate tetrahydrate in water (Aldrich, 1.0 M in Mo) and 1 mL of $Pb(NO_3)_2$ in water (Aldrich, 0.1 M) were added. The slurry was heated on a hot plate at 80–100° C. for 5 min., then 10 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 300° C. at 3° C./min and held at 300° C. for 1 hour in air and 1 hour in Ar, then heated in Ar from 300 to 575° C. at 10° C./min and held at 575° C. for 2 hours. The final catalyst had a nominal composition of $Pb_{0.25}MoV_{0.5}Te_{0.33}O_x$. The catalyst thus obtained was pressed in a mold and then broken and sieved to 10–20 mesh granules for reactor evaluation.

Example 24

To a 100 mL Pyrex beaker, 1.06 g of tellurium dioxide (Aldrich), 20 mL of ammonium heptamolybdate tetrahydrate in water (Aldrich, 1.0 M in Mo) and 0.2 mL of $Au(OH)_3$ in water (Aldrich, 0.1 M) were added. The mixture was heated on a hot plate at 80–100° C. for 5 min., then 10 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 300° C. at 3° C./min and held at 300° C. for 1 hour in air and 1 hour in Ar, then heated in Ar from 300 to 575° C. at 10° C./min and held at 575° C. for 2 hours. The final catalyst had a nominal composition of $Au_{0.025}MoV_{0.5}Te_{0.33}O_x$. The catalyst thus obtained was pressed in a mold and then broken and sieved to 10–20 mesh granules for reactor evaluation.

Comparative Example 2

To a 45 mL Parr Acid Digestion Bomb with an inner tube made of PTFE, 0.93 g of $Sb_2(SO_4)_3$ (Aldrich) and 21 mL of ammonium heptamolybdate tetrahydrate in water (Aldrich, 1.0 M in Mo) were added. The mixture was first hydrothermally treated at 150° C. for 30 min., and then 7 mL of vanadyl sulfate hydrate in water (Aldrich, 1.0 M in V) were added to the bomb at 80° C. with stirring. The bomb contents were hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 300° C. at 3° C./min and held at 300° C. for 1 hour in air and 1 hour in Ar, then heated in Ar from 300 to 575° C. at 10° C./min and held at 575° C. for 2 hours. The final catalyst had a nominal composition of $MoV_{0.33}Sb_{0.17}O_x$. The catalyst thus obtained was pressed in a mold and then broken and sieved to 10–20 mesh granules for reactor evaluation.

Comparative Example 3

To a 100 mL Pyrex beaker, 1.06 g of $Sb_2(SO_4)_3$ (Aldrich) and 24 mL of ammonium heptamolybdate tetrahydrate in water (Aldrich, 1.0 M in Mo) were added. The mixture was heated on a hot plate at 80–100° C. for 5 min., then 8 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 0° C./min and held at 275° C. for 1 hour, then in Ar from 275 to 575° C. at 2° C./min and held at 575° C. for 2 hours. The final catalyst had a nominal composition of $MoV_{0.33}Sb_{0.17}O_x$. The catalyst thus obtained was pressed in a mold and then broken and sieved to 10–20 mesh granules for reactor evaluation.

Example 25

To a 100 mL Pyrex beaker, 0.93 g of $Sb_2(SO_4)_3$ (Aldrich), 21 mL of ammonium heptamolybdate tetrahydrate in water (Aldrich, 1.0 M in Mo) and 1 mL of $VF_3$ in water (Aldrich, 0.1 M in F) were added. The mixture was heated on a hot plate at 80–100° C. for 5 min., then 7 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 575° C. at 2° C./min and held at 575° C. for 2 hours. The final catalyst had a nominal composition of $F_{0.025}MoV_{0.33}Sb_{0.17}O_x$. The catalyst thus obtained was pressed in a mold and then broken and sieved to 10–20 mesh granules for reactor evaluation.

Example 26

To a 100 mL Pyrex beaker, 0.93 g of $Sb_2(SO_4)_3$ (Aldrich), 21 mL of ammonium heptamolybdate tetrahydrate in water (Aldrich, 1.0 M in Mo) and 1 mL of $Au(OH)_3$ in water (Aldrich, 0.1 M) were added. The mixture was heated on a hot plate at 80–100° C. for 5 min., then 10 mL of vanadyl sulfate hydrate in water (Aldrich, 1.0 M in V) were added and the mixture was heated for another 5 min. at the same temperature. The beaker contents were transferred to a 45 mL Parr Acid Digestion Bomb with an inner tube made of PTFE and was hydrothermally treated at 175° C. for 20 hours. Black solids formed on the wall and bottom of the bomb were collected by gravity filtration, washed with deionized water (50 mL), dried in a vacuum oven at 25° C. overnight, and then calcined in air from 25 to 275° C. at 10° C./min and held at 275° C. for 1 hour, then in Ar from 275 to 575° C. at 2° C./min and held at 575° C. for 2 hours. The final catalyst had a nominal composition of $Au_{0.025}MoV_{0.33}Sb_{0.17}O_x$. The catalyst thus obtained was pressed in a mold and then broken and sieved to 10–20 mesh granules for reactor evaluation.

EVALUATION AND RESULTS

Catalysts were evaluated in a 10 cm long Pyrex tube reactor (internal diameter: 3.9 mm). The catalyst bed (4 cm long) was positioned with glass wool at approximately mid-length in the reactor and was heated with an electric furnace. Mass flow controllers and meters regulated the gas flow rate. The oxidation was conducted using a feed gas stream of propane, steam and air, with a feed ratio of propane:steam:air of 1:3:96. The reactor effluent was analyzed by a FTIR. The results at a 3 second residence time are shown in Tables 1–4.

TABLE 1

| Catalyst | Composition | Temp. ° C. | % C3 Conv. | % AA yield |
| --- | --- | --- | --- | --- |
| Comp. Ex. 1 | $MoV_{0.5}Te_{0.17}O_x$ | 393 | 27 | 2 |
| Ex. 1 | $Ga_{0.025}MoV_{0.5}Te_{0.17}O_x$ | 372 | 35 | 6 |
| Ex. 2 | $Br_{0.005}MoV_{0.5}Te_{0.17}O_x$ | 402 | 51 | 7 |
| Ex. 3 | $F_{0.005}MoV_{0.5}Te_{0.17}O_x$ | 284 | 29 | 12 |
| Ex. 4 | $Bi_{0.005}MoV_{0.5}Te_{0.17}O_x$ | 366 | 23 | 5 |
| Ex. 5 | $I_{0.005}MoV_{0.5}Te_{0.17}O_x$ | 376 | 25 | 7 |
| Ex. 6 | $Ge_{0.005}MoV_{0.5}Te_{0.17}O_x$ | 366 | 36 | 11 |
| Ex. 7 | $La_{0.025}MoV_{0.5}Te_{0.17}O_x$ | 384 | 42 | 8 |
| Ex. 8 | $Y_{0.005}MoV_{0.5}Te_{0.17}O_x$ | 385 | 42 | 11 |
| Ex. 9 | $Y_{0.005}MoV_{0.5}Te_{0.33}O_x$ | 385 | 40 | 13 |
| Ex. 10 | $Ag_{0.025}MoV_{0.5}Te_{0.17}O_x$ | 403 | 24 | 4 |
| Ex. 11 | $Zn_{0.005}MoV_{0.5}Te_{0.17}O_x$ | 393 | 39 | 6 |
| Ex. 12 | $Au_{0.001}MoV_{0.5}Te_{0.17}O_x$ | 385 | 28 | 10 |
| Ex. 13 | $As_{0.005}MoV_{0.5}Te_{0.17}O_x$ | 393 | 56 | 9 |
| Ex. 14 | $Pb_{0.005}MoV_{0.5}Te_{0.17}O_x$ | 384 | 36 | 12 |
| Ex. 15 | $Se_{0.001}MoV_{0.5}Te_{0.17}O_x$ | 403 | 27 | 3 |

TABLE 2

| Catalyst | Composition | Temp. ° C. | % C3 Conv. | % AA yield |
| --- | --- | --- | --- | --- |
| Ex. 16 | $MoV_{0.33}Te_{0.33}O_x$ | 368 | 56 | 27 |
| Ex. 16 | $MoV_{0.33}Te_{0.33}O_x$ | 400 | 78 | 20 |
| Ex. 17 | $MoV_{0.33}Te_{0.33}O_x$ | 394 | 52 | 29 |
| Ex. 18 | $MoV_{0.5}Te_{0.33}O_x$ | 396 | 56 | 30 |
| Ex. 19 | $MoV_{0.5}Te_{0.5}O_x$ | 381 | 50 | 31 |

TABLE 3

| Catalyst | Composition | Temp. ° C. | % C3 Conv. | % AA yield |
| --- | --- | --- | --- | --- |
| Ex. 20 | $Cl_{0.025}MoV_{0.5}Te_{0.33}O_x$ | 357 | 65 | 26 |
| Ex. 21 | $As_{0.025}MoV_{0.5}Te_{0.33}O_x$ | 390 | 44 | 25 |
| Ex. 22 | $As_{0.025}MoV_{0.5}Te_{0.33}O_x$ | 369 | 48 | 21 |
| Ex. 23 | $Pb_{0.025}MoV_{0.5}Te_{0.33}O_x$ | 369 | 34 | 21 |
| Ex. 24 | $Au_{0.025}MoV_{0.5}Te_{0.33}O_x$ | 387 | 29 | 14 |

TABLE 4

| Catalyst | Composition | Temp. ° C. | % C3 Conv. | % AA yield |
| --- | --- | --- | --- | --- |
| Comp. Ex. 2 | $MoV_{0.33}Sb_{0.17}O_x$ | 402 | 97 | 6 |
| Comp. Ex. 3 | $MoV_{0.33}Sb_{0.17}O_x$ | 393 | 64 | 1 |
| Ex. 25 | $F_{0.025}MoV_{0.33}Sb_{0.17}O_x$ | 260 | 21 | 8 |
| Ex. 26 | $Au_{0.025}MoV_{0.33}Sb_{0.17}O_x$ | 241 | 13 | 8 |

What is claimed is:

1. A process for producing an unsaturated carboxylic acid which comprises subjecting an alkane, or a mixture of an alkane and an alkene, to a vapor phase catalytic oxidation reaction in the presence of a catalyst comprising a mixed metal oxide having the empirical formula $$Mo_aV_bM_cX_dO_e$$

wherein M is an element selected from the group consisting of Te, Sb and Nb,
wherein X is an element selected from the group consisting of Sc, Y, La, Re, Ir, Cu, Ag, Au, Zn, Ga, Si, Ge, As, Pb, S, Se, Sn, Bi, F, Cl, Br and I, and
wherein, when a=1, b=0.01 to 1.0, c=0.01 to 1.0, d=0 to 1 and e is dependent on the oxidation state of the other elements;
with the proviso that, when d=0, M is selected from the group consisting of Nb and Te, and
with the further proviso that, when d=0 and M=Te, $0.01 \leq b < 0.50$ or $0.17 < c \leq 1.0$.

2. The process for producing an unsaturated carboxylic acid according to claim 1, wherein said catalyst is produced by a synthesis process comprising:
 (i) admixing compounds of elements Mo, V, M and X, as needed, and a solvent comprising water to form a first admixture containing at least 2 but less than all of said elements Mo, V, M and X;
 (ii) heating said first admixture at a temperature of from 80° C. to 150° C. for from 5 minutes to 48 hours;
 (iii) then, admixing compounds of elements Mo, V, M and X, as needed, with said first admixture to form a second admixture containing elements Mo, V, M and X, in the respective atomic proportions a, b, c and d, wherein, when a=1, b=0.01 to 1.0, c=0.01 to 1.0 and d=0 to 1;
 (iv) heating said second admixture at a temperature of from 50° C. to 300° C. for from 1 hour to several weeks, in a closed vessel under pressure;
 (v) recovering insoluble material from said closed vessel to obtain a catalyst.

3. The process for producing an unsaturated carboxylic acid according to claim 2, wherein said synthesis process further comprises calcining said recovered insoluble material.

4. The process for producing an unsaturated carboxylic acid according to claim 3, wherein said calcination comprises heating said recovered insoluble material to a first temperature in an oxidizing atmosphere, then heating the so-treated recovered insoluble material from said first temperature to a second temperature in a non-oxidizing atmosphere.

5. The process for producing an unsaturated carboxylic acid according to claim 2, wherein said first admixture comprises the elements Mo, M and X.

6. The process for producing an unsaturated carboxylic acid according to claim 5, wherein M=Te.

* * * * *